US005645555A

United States Patent [19]
Davis et al.

[11] Patent Number: 5,645,555
[45] Date of Patent: Jul. 8, 1997

[54] ROTARY LANCET

[75] Inventors: Richard Micheal Davis, Guntersville; Stephen P. Lisak, Arab; Rowland W. Kanner, Guntersville, all of Ala.

[73] Assignee: Ryder International Corporation, Arab, Ala.

[21] Appl. No.: 515,161

[22] Filed: Aug. 15, 1995

Related U.S. Application Data

[63] Continuation of Ser. No. 281,065, Jul. 27, 1994, Pat. No. 5,476,474.
[51] Int. Cl.⁶ ................................................. A61B 17/32
[52] U.S. Cl. ................................................. 606/182; 128/770
[58] Field of Search ................................... 606/181–183; 128/770

[56] References Cited

U.S. PATENT DOCUMENTS 5,133,730  7/1992  Biro et al. ............................. 606/182

FOREIGN PATENT DOCUMENTS 0192443  8/1986  European Pat. Off. ............... 606/182

*Primary Examiner*—Guy V. Tucker
*Assistant Examiner*—William Lewis
*Attorney, Agent, or Firm*—Trexler, Bushnell, Giangiorgi & Blackstone, Ltd.

[57] ABSTRACT

A lancet actuator device and mechanism for sequentially advancing and retracting a lancet blade include a housing having an opening for operating projection of the lancet blade. The actuator mechanism includes a drive spring structure insertably mounted in the housing and arranged to drive pivotal motion of the lancet blade including sequential thrusting of the blade from the housing aperture followed by immediate pivotally reverse retracting of the blade from the aperture into the housing as the spring deengerizes.

16 Claims, 3 Drawing Sheets

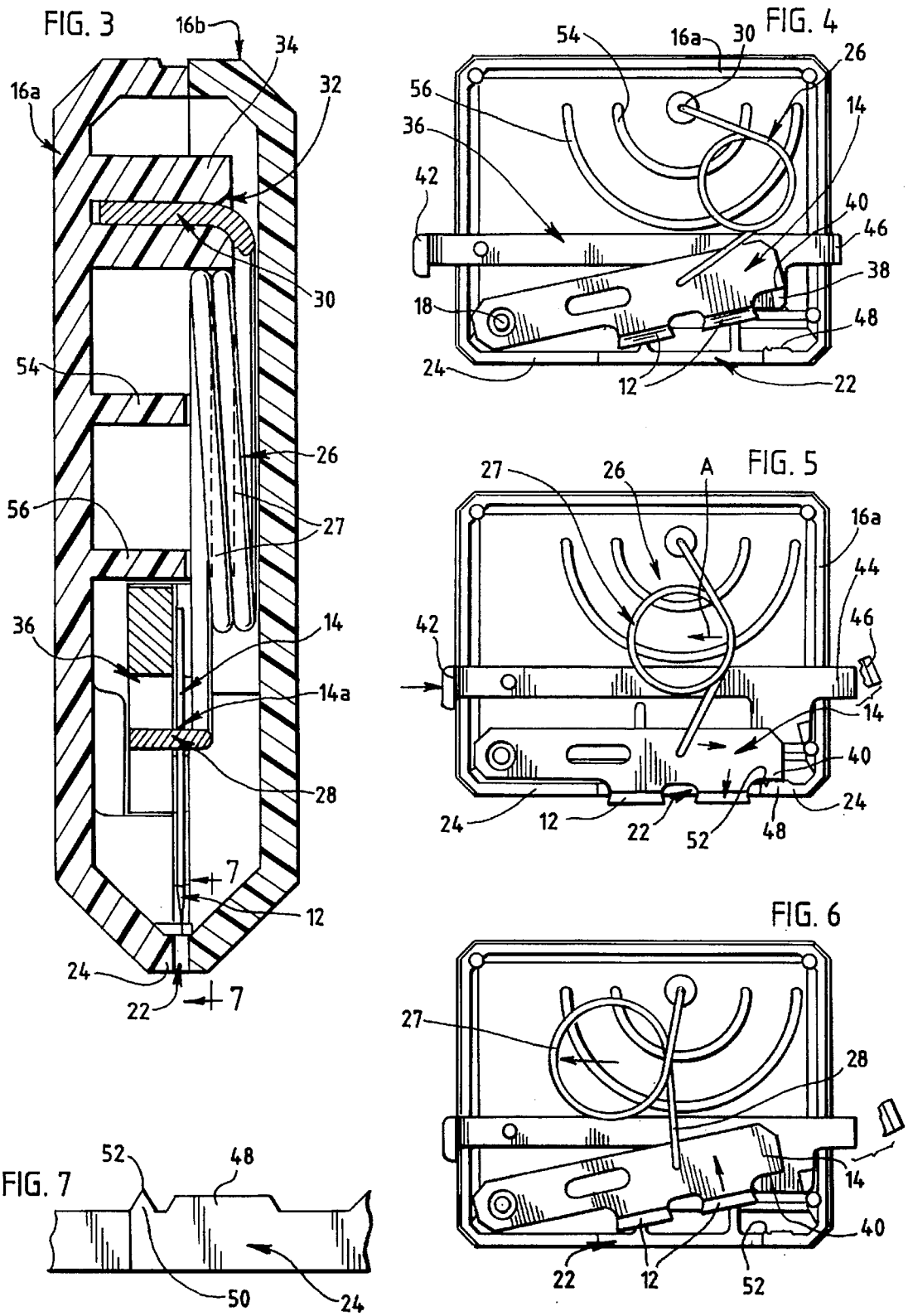

ROTARY LANCET

This is a continuation of application(s) Ser. No. 08/281,065 filed on Jul. 27, 1994, now U.S. Pat. No. 5,476,474.

BACKGROUND OF THE INVENTION

This invention relates to lancet devices for particular use in skin incision procedures particularly to determine bleeding time elapsed before proper platelet aggregation, and more particularly to disposable devices for actuating the skin incision procedure.

In order to reduce trauma to the patient during skin incision procedures, automated lancet devices have been developed which eliminate the patient's view of both the skin incision and the lancet blade itself. As described, for example, in U.S. Pat. Nos. 4,078,552; 4,628,929; 4,735,203, the lancet blade can be housed within a small device which provides a spring-driven mechanism for thrusting and retracting the blade. While such devices obstruct the patient's view, the linear blade path produces a cleaving action and limited control over the depth of incision, as well as considerable patient discomfort and required healing. U.S. Pat. No. 5,133,730 describes a lancet device in which a drive spring is integrally molded with a living hinge in the molded housing, as well as an integrally molded trigger. The integral spring is arranged to produce a rotary lancet blade motion enabling a cleaner, slicing incision, however, the integral spring and blade retraction structure require complex molding and manufacture of the devices.

These and other disadvantages are eliminated by the lancet actuator mechanism in accordance with the present invention.

SUMMARY OF THE INVENTION

In accordance with the present invention, a lancet actuator device and mechanism for sequentially advancing and retracting a lancet blade include a housing having an opening for operating projection of the lancet blade. The actuator mechanism includes a drive spring structure insertably mounted in the housing and arranged to drive pivotal motion of the lancet blade including sequential thrusting of the blade from the housing aperture followed by immediate pivotally reverse retracting of the blade from the aperture into the housing as the spring deenergizes.

In preferred embodiments of the lancet actuator, a torsion spring bears upon and drives both the pivotal thrusting and retracting motion of the blade structure. In particular preferred embodiments, the lancet actuator device is constructed for single use disposibility and assembled with the torsion spring in pre-stressed condition and a manual trigger structure which blocks pivotal motion of the blade structure until the skin penetration operation is initiated. Following a single skin penetration operation, the unwound torsion spring retains the retracted blade within the housing for handling safety in disposal.

A "telltale" indicator of lancet mechanism operation is provided by a formation on the housing which leaves an impression of impact by the blade during its operative rotary motion.

BRIEF DESCRIPTION OF THE DRAWINGS

FIG. 3 is an enlarged sectional view along a plane indicated by line 3—3 in FIG. 1;

FIGS. 4–6 are sequential views of the operating positions of the assembled actuator mechanism shown in FIGS. 1–3;

FIG. 7 is an enlarged fragmentary sectional view along a plane indicated by line 7—7 in FIG. 3.

DETAILED DESCRIPTION OF THE PREFERRED EMBODIMENTS

Figure 1:
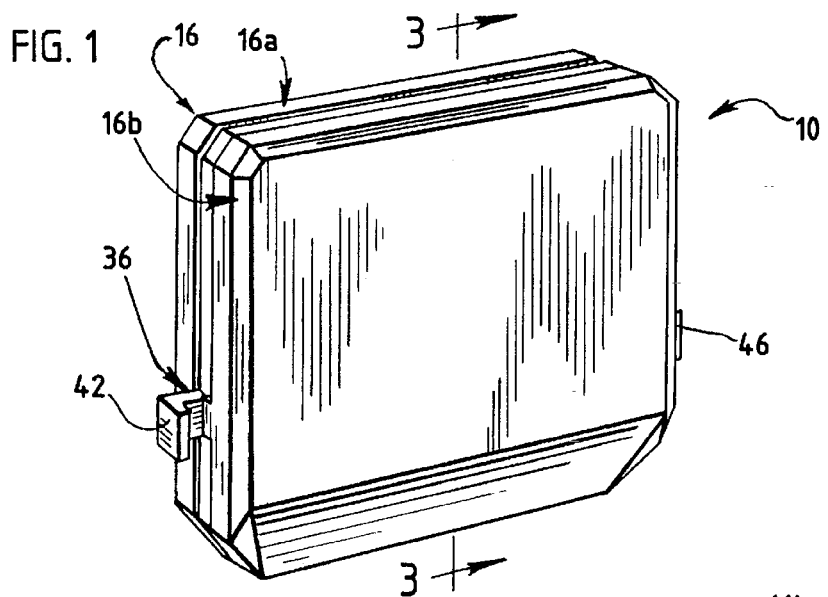
FIG. 1 is a perspective view of one embodiment of the assembled lancet actuator and device in accordance with the present invention.
Figure 2:
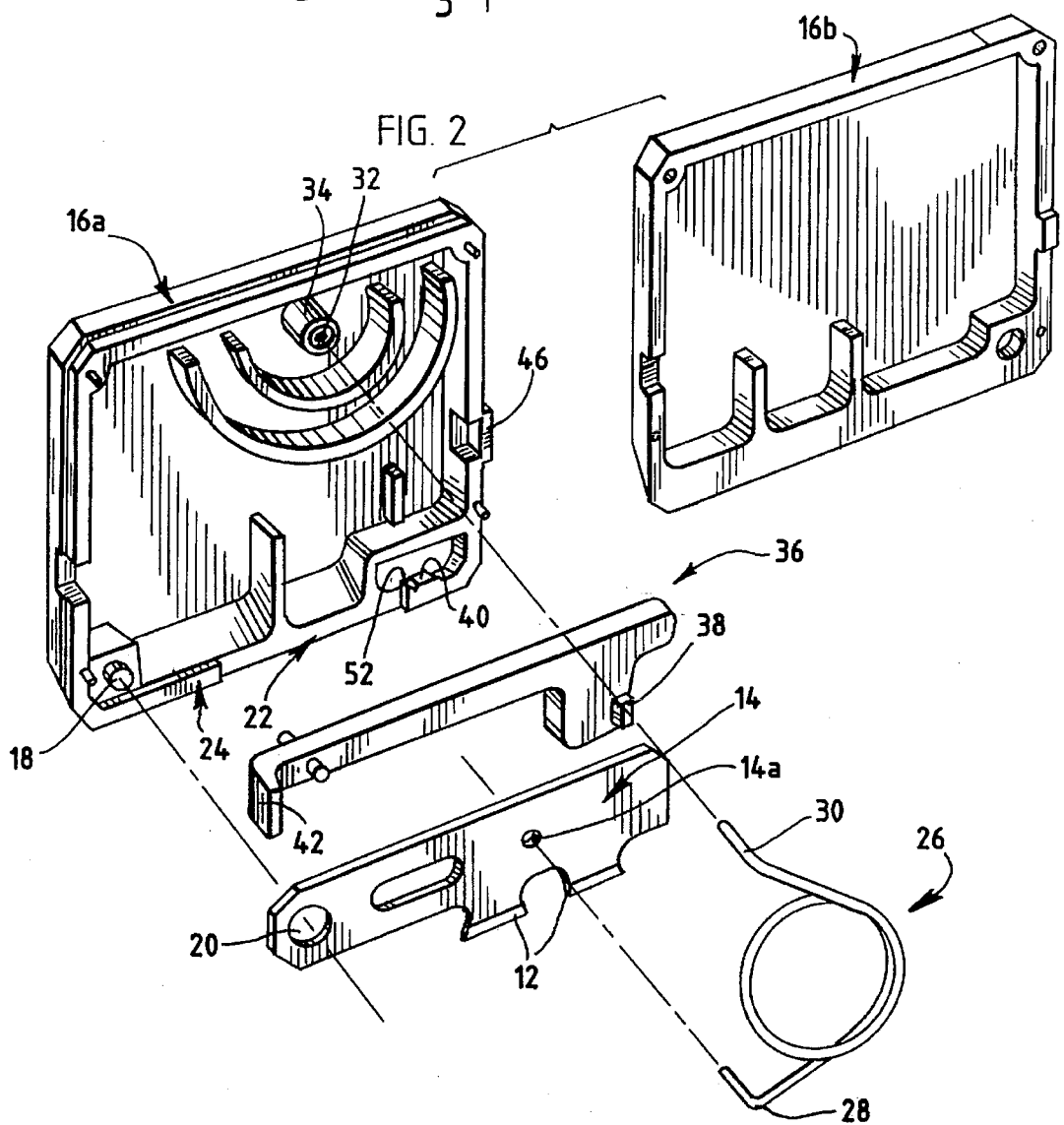
FIG. 2 is an exploded perspective view of the assembled actuator shown in FIG. 1.
Figure 8:
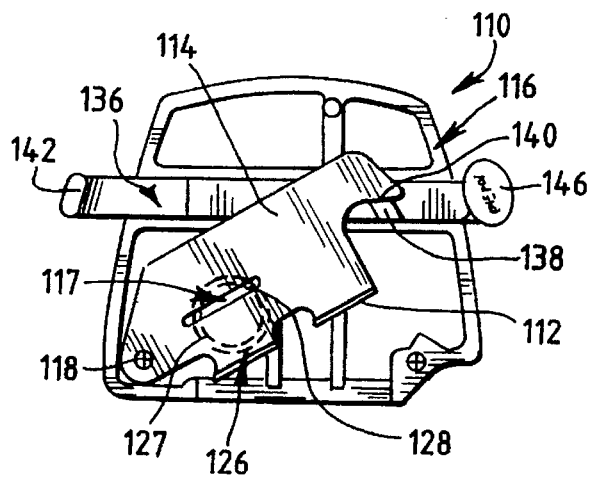
FIG. 8–11 are internal views of a second embodiment of a lancet actuator in accordance with the present insertion and illustrate sequential operating positions of the actuator mechanism.

Referring to FIGS. 1 and 2, an embodiment of a lancet actuator assembly in accordance with the present invention is generally designated by reference character 10. The illustrated embodiment of actuator 10 is designed for single-use dispositibility and employs a pre-loaded, sterilized lancet blade, 12,12 which is integrally formed on a carrier arm 14. The carrier arm 14 is pivotally mounted within the vertically split molded housing 16, by means of a pivot bearing pin 18 which extends through an aperture 20 in the carrier arm 14. The housing portion 16a has an opening slot 22 in the bottom wall 24 through which the pivoting lancet blade 12,12 is driven to project in the skin incision operation as described hereinafter.

In the illustrated embodiment, the pivotal motion of the blade 12 and carrier 14 is driven by a torsion spring generally designated 26 which has an end arm 28 coupled to bear on the carrier arm 14 by insertion through a hole 14a and the opposite end arm 30 is rotatably anchored by insertion through a journal bore 32 in a boss 34 internally projecting from the housing portion 16a as particularly shown in FIGS. 2 and 3. In the illustrated embodiment of the lancet actuator 10, the torsion spring 26 is pre-stressed in the position of configuration shown in FIG. 4 and imposes force urging the carrier 14 downwardly toward the opening slot 22, however in the preoperational position as shown in FIG. 4, the downward biasing force is releasably restrained by a trigger arm generally designated 36 which has a depending and laterally extending foot stop 38 against which the lower nose surface 40 of the lade carriage 14 is releasably abutted and retained.

In operation of the illustrated embodiment of the lancet actuator 10, the "pre-cocked" actuator 10 (FIG. 4) is placed so that the bottom wall 24 engages the target skin (not shown) of the patient. The skin penetration operation is initiated by manually depressing the projecting trigger end 42 of the trigger member 36 which will displace the trigger member 36 to the right from the position shown in FIG. 4 to the position shown in FIG. 5 so that the opposite trigger end 44 impacts and detaches the frangible, breakaway tab 46 integrally formed on the housing portion 16a. Absence of this breakaway tab from the actuator 10 will indicate that the device has been used (perhaps only triggered) and is to be discarded. Primarily, the displacement of the trigger member 36 also moves the foot stop 38 therewith which releases engagement by the carrier surface 40 enabling the biasing force from the spring 26 to downwardly propel and pivot the blade carriage 14 and project the blade 12 through the opening slot 22 to the skin incision extension position of FIG. 5. The rotary motion of the blade 12 produces a slicing skin incision as opposed to a linear cleaving action, and the rotary slicing produces a cleaner incision and healing of the skin as well as improvement in the coagulation timing determination.

Referring again to FIG. 5, thrusting of the blade 12 and maximum extension thereof through the housing wall slot 22 defining precise skin incision depth is controlled by a blade contact stop surface 48 on the interior of the housing bottom wall 24 which receives impact by the carrier nose surface 40 to block further blade thrust. Additionally, the housing bottom wall 24 also has an upwardly projecting rib 50 terminating in an apex 52 which upwardly projects slightly beyond the stop surface 48 and is therefore crushed or blunted from impact by the carrier nose surface 40 prior to impact thereof against the stop surface 48; the crushed apex 52 thereby serves a "telltale" indicator that the actuator 10 has been triggered and the rotary motion of the carrier 14 has previously operated correctly.

From the position in FIG. 5, continued unwinding force of the spring 26 bearing upon the momentarily stopped thrusting of the blade carrier 14 at maximum incision depth also produces a reactionary force indicated by arrow A which maintains a generally clockwise momentum and pivot of the coil portion 27 of the torsion spring 26 which automatically induces a sequentially continuous reversal in the motion of the carrier 14. This motion reversal retracts the blade 12 inwardly withdrawing into the housing from the slot 22 as the continued leftward momentum of the spring coil portion 27 into the position shown in FIG. 6 allows the spring arm 28 to pull on and draw the reverse pivot of the carrier 14 and blade 12 upwardly into the housing portion 16a. Two arcuate guide flanges 54 and 56 internally project from the housing portion 16a and provide inner surface for a stabilized sliding of the spring coil 27 thereagainst on its rotary path during the operational uncoiling in the skin incision operation, as well as preventing any potential twisting of the unwinding coil portion 27.

In the illustrated embodiment of the actuator 10, the blade 12 can only project from the housing slot 22 during a single, deliberately triggered operation, because the entirely enclosed drive mechanism prevents any re-winding of the spring 26, so that after a single skin incision operation, the lancet assembly 10 cannot be re-cocked or reused and will be discarded, effectively preventing any cross-contamination of blood. In addition, following a single operation of the actuator 10, the unwound condition of the spring 26 maintains the internal, pivotally retracted position of the carrier 14 and blade 12 as shown in FIG. 6 in which the terminally residual coiling of coil portion 27 restrains the carrier 14 against a second thrusting of the carrier 14 toward the housing slot 22, and the blade 12 cannot be exposed from the housing which prevents any hazard to handling for disposal of the actuator 10.

Figure 9:
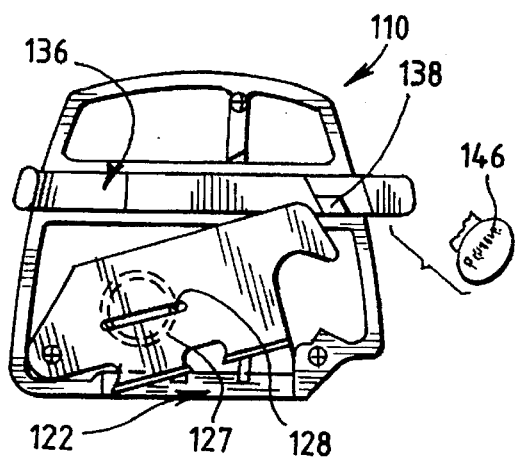
Figure 10:
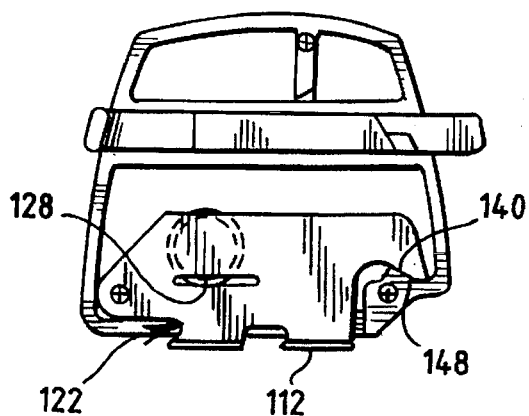
Figure 11:
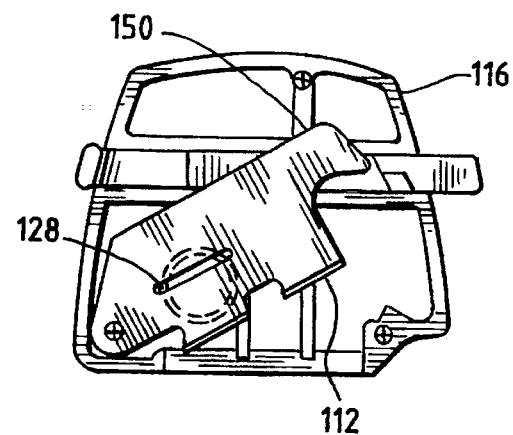

Referring now to FIGS. 9-11, a modified embodiment of a lancet actuator assembly 110 in accordance with the invention is illustrated in which the blade carrier 114 has an elongate slot 117 which is only slightly wider than the diameter of one end leg 128 inserted therethrough from a torsion drive spring 126. The opposite spring end (not shown) is fixed to the split housing portion 116. In the pre-cocked assembly 110, the spring end 128 bears on the lower edge of the slot 117 to impose a rotary downward bias force on the blade carrier 114 which can pivot on the housing pivot pin 118 but is initially restrained by abutment of the nose surface 140 against the retainer foot 138 formed on the trigger member 136.

In operation, a frangible safety tab 146 formed on the housing 116 is manually detached to unblock the path of the trigger member 136 which can then be depressed to displace the stop 138 and release the rotary motion of the blade carrier 114 as shown in FIG. 9. Unwinding of the drive spring coil 127 propels the spring end 128 from right to left through the carrier slot 117 and at the same time, the spring end 128 drives the downward rotary motion of the carrier 114 from the position shown in FIG. 9 to the position shown in FIG. 10 in which the blade 112 is thrusted through the lower housing wall slot 122, whereupon the carrier nose surface 140 impacts the housing stop surface 148 to terminate maximum rotary thrust and define the skin incision depth of the blade 112. Continued unwinding of the spring coil portion 127 produces a reversal and upward force of the spring end 128 against the upper edge of the blade carrier slot 117 as the spring end 128 continues travel therethrough, resulting in sequentially continuous reversal in the pivotal motion of the carrier 114 so that it retracts the blade 112 into the housing 116 in withdrawal from the slot 122. Residual unwinding force imposed by the spring coil 127 maintains the blade carrier against a return stop surface 150 internally formed on the housing 116. Since the torsion spring cannot be rewound, the actuator 110 is again designed for single use disposibility. Additionally, an indicator of previous operation, for example, an impact "telltale" similar to that of the first actuator embodiment 10 can be provided (not shown).

While preferred embodiments of the present invention is shown and described, it is envisioned that those skilled in the art may devise various modifications and equivalents without departing from the spirit and scope of the appended claims.

The invention claimed is:

1. A lancet actuator for sequentially advancing and retracting a lancet blade in a skin penetration operation, comprising:
   a housing containing a lancet blade structure and having an aperture for projection therethrough of a blade portion of the blade structure;
   spring means insertably mounted in said housing and arranged to drive pivotal motion of said blade structure and blade portion, said blade structure continuously pivoting on a pivot without translation relative thereto throughout both sequential pivotal thrusting of said blade portion from said aperture followed by immediate pivotal retracting of the blade portion from said aperture into said housing during said pivotal motion of said blade structure.

2. A lancet actuator according to claim 1 wherein said spring means bears upon said blade structure.

3. A lancet actuator according to claim 1 further comprising trigger means for initiating propulsion by said spring means to drive said blade structure pivot motion.

4. A lancet actuator according to claim 3 wherein said trigger means comprises a manually deflectable trigger member having a retaining portion releasably blocking pivot of said blade structure until manual deflection in said skin penetration operation.

5. A lancet actuator according to claim 1 further comprising retainer means for retaining said blade portion internal to said housing following said thrusting and retracting in a single skin penetration operation of said lancet actuator.

6. A lancet actuator according to claim 1 wherein said said spring means in deenergized condition thereof bearing upon said blade carriage retains said blade portion internal to said housing following said thrusting and retracting in a single skin penetration operation of said lancet actuator.

7. A lancet actuator for sequentially advancing and retracting a lancet blade in a skin incision operation, comprising:
   a housing containing a lancet blade carriage and having an aperture for projection therethrough of a blade portion on the blade carriage; and a torsion spring mounted in said housing and arranged to drive pivotal motion of said blade carriage and blade portion, said blade structure continuously pivoting on a pivot without translation relative thereto throughout both sequential pivotal thrusting of said blade portion from said aperture followed by immediate pivotal retracting of the blade portion from said aperture into said housing during said pivotal motion of said blade structure.

8. A lancet actuator according to claim 7 further comprising trigger means for initiating uncoiling of said torsion spring to drive said blade pivot motion.

9. A lancet actuator according to claim 7 wherein said torsion spring bears upon said blade structure.

10. A lancet actuator according to claim 9 wherein said trigger means comprises a manually deflectable trigger member having a retaining portion releasably blocking pivot of said blade structure until manual deflection in said skin penetration operation.

11. A lancet actuator according to claim 7 wherein said torsion spring in deenergized condition thereof bearing on said blade carriage retains said blade portion internal to said housing following a single skin penetration operation of said lancet actuator.

12. A lancet actuator for skin penetration operation, comprising: a displaceable blade structure arranged for thrusting into a skin penetration position; and a blade impact impression structure including a deformable surface arranged on said actuator in a displacement path of said blade structure and having a configuration to deform and to produce an impression of impact thereagainst by said blade structure, thereby serving as an indicator on said actuator of the blade structure displacement.

13. A lancet actuator according to claim 12 wherein said impact comprises a generally pointed surface capable of distortion upon impact by said blade structure to define said impact impression thereof.

14. A lancet actuator according to claim 12 further comprising a housing means containing said blade structure and having said impact impression structure formed thereon.

15. A lancet actuator according to claim 14 wherein said impact impression structure is internally formed on said housing means.

16. A lancet actuator according to claim 15 wherein said impact comprises an apex formed within said housing and capable of blunting by impact from said blade structure to produce indicator thereof.

* * * * *